United States Patent
Jensen et al.

(10) Patent No.: US 6,656,123 B2
(45) Date of Patent: Dec. 2, 2003

(54) COMBINED FUNDAMENTAL AND HARMONIC ULTRASONIC IMAGING AT LOW MI OR DEEPER DEPTHS

(75) Inventors: Seth E. Jensen, Bothell, WA (US); Michalakis Averkiou, Kirkland, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/026,997

(22) Filed: Dec. 19, 2001

(65) Prior Publication Data

US 2003/0114758 A1 Jun. 19, 2003

(51) Int. Cl.[7] .................................................. A61B 8/14
(52) U.S. Cl. ..................................................... 600/458
(58) Field of Search ............................... 600/407, 437, 600/438, 440–447, 449–458; 73/625, 626; 128/916; 367/7, 11, 130, 138

(56) References Cited

U.S. PATENT DOCUMENTS

| 5,724,976 A |   | 3/1998 | Mine |         |
|---|---|---|---|---|
| 5,833,613 A |   | 11/1998 | Averkiou et al. |         |
| 5,879,303 A |   | 3/1999 | Averkiou et al. |         |
| 5,951,478 A |   | 9/1999 | Hwang et al. |         |
| 6,102,865 A | * | 8/2000 | Hossack et al. | 600/459 |
| 6,104,670 A | * | 8/2000 | Hossack et al. | 367/7 |
| 6,108,572 A | * | 8/2000 | Panda et al. | 600/407 |
| 6,117,082 A |   | 9/2000 | Bradley |         |
| 6,171,246 B1 |   | 1/2001 | Averkiou et al. |         |
| 6,186,950 B1 |   | 2/2001 | Averkiou et al. |         |
| 6,206,833 B1 | * | 3/2001 | Christopher | 600/443 |
| 6,283,919 B1 |   | 9/2001 | Roundhill et al. |         |

\* cited by examiner

*Primary Examiner*—Ali M. Imam
(74) *Attorney, Agent, or Firm*—W. Brinton Yorks, Jr.

(57) ABSTRACT

An ultrasonic imaging apparatus and method are described for imaging nonlinear response objects such as contrast agents at greater depths. Transmit pulses include two fundamental frequency components, one of which is to produce harmonic components at the fundamental frequency of the other component. In the presence of a contrast agent these harmonic components are used for imaging the contrast agent. When the contrast agent is not present imaging is performed using the fundamental echoes of the other echo frequency. Preferably the harmonic frequency of the first fundamental component is aligned with the second fundamental frequency. The technique is especially useful when imaging contrast agents at low MI and at significant depths in the body.

21 Claims, 3 Drawing Sheets

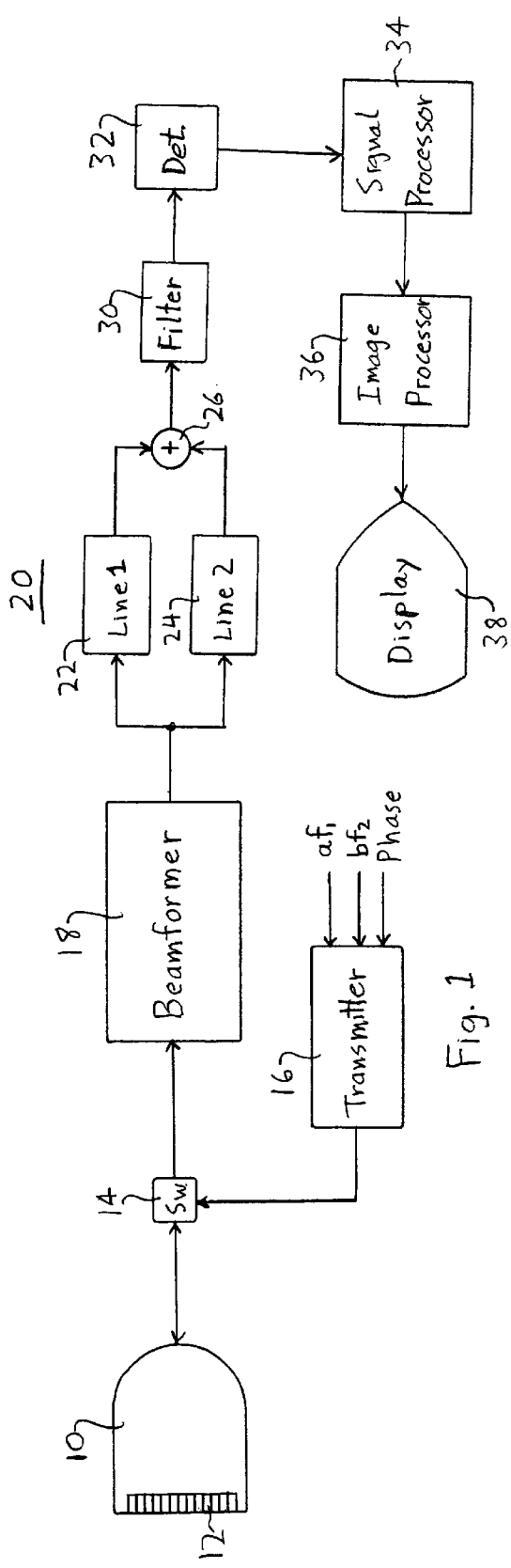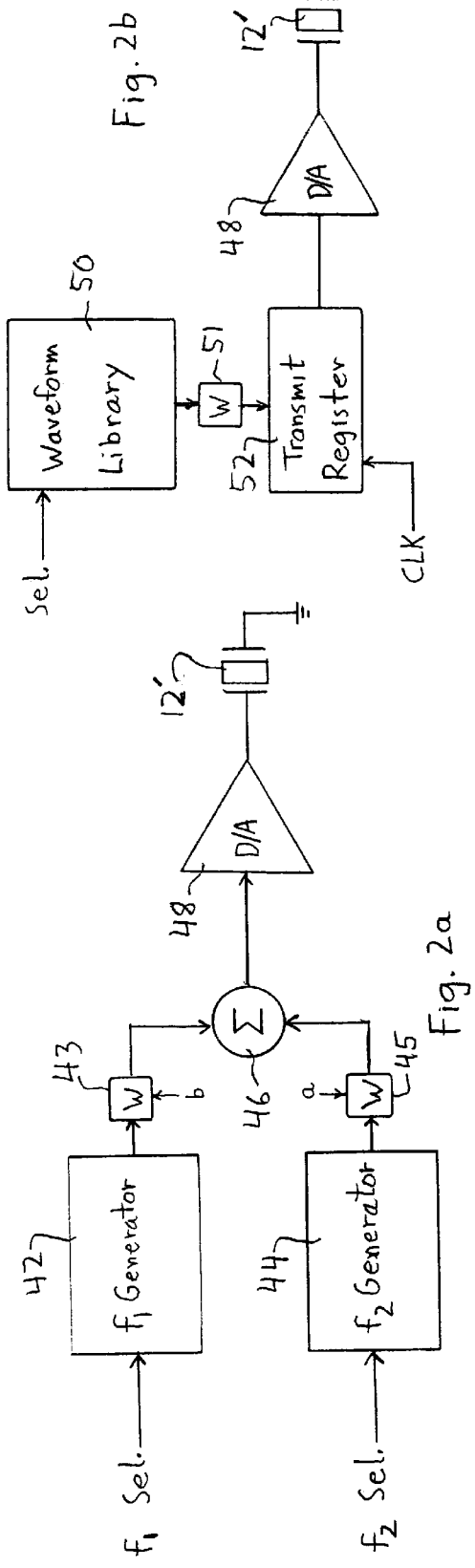

COMBINED FUNDAMENTAL AND HARMONIC ULTRASONIC IMAGING AT LOW MI OR DEEPER DEPTHS

This invention relates to ultrasonic diagnostic imaging systems and, in particular, to ultrasonic diagnostic imaging systems which utilize both fundamental and harmonic ultrasonic signals for imaging.

In ultrasonic harmonic imaging, two dimensional (2D) or three dimensional (3D) images are formed by transmitting ultrasound at one frequency (or range of frequencies) and receiving at this frequency and higher harmonics of the transmit frequency. These harmonic signals are generated either by scattering from microbubbles of a harmonic contrast agent as described in U.S. Pat. No. 5,833,613 or by non-linear propagation in tissue (tissue harmonic imaging, or THI) as described in U.S. Pat. No. 5,879,303. Typically, receive beams are formed only from the second harmonic echo signals, with the transmitted (or "fundamental") echo signals being removed either by filtering or by cancellation techniques such as pulse inversion. See U.S. Pat. No. 5,951,478. For THI, adequate removal of the fundamental signal is essential for the improvements in clutter suppression and contrast resolution which are typically seen.

Under some circumstances it may be of interest to image with both the 2nd harmonic signal and the fundamental signal which would normally be discarded in harmonic imaging. For example, two of the limitations of THI are poor near-field imaging (before non-linear propagation has had a chance to generate a significant 2nd harmonic response) and poor penetration, because the higher frequency 2nd harmonic echo is highly attenuated as compared to the fundamental echo signal. One option for addressing this problem is to image with the fundamental signal in the near and far fields while imaging the 2nd harmonic in the mid-field. See, for example, U.S. Pat. No. 6,283,919 which teaches the formation of ultrasonic images which are a blend of fundamental and harmonic signals. U.S. Pat. No. 6,514,206 describes an ultrasound system and method for doing fundamental and harmonic imaging simultaneously. In the system shown in this patent application a fundamental signal is transmitted from a low end of the transducer passband and harmonic signals are received at an upper end of the passband. Fundamental signals are also sent and received from the center of the transducer passband, the optimal band of the transducer. Images are formed using the received harmonic signals and the optimally centered fundamental signals.

An application which would benefit from a combination of fundamental and harmonic imaging is contrast agent imaging at deep depths within the body. For example, a clinician may be trying to image the vasculature of a tumor deep within the liver. Initially the clinician must locate the tumor so that it can be visually monitored as the contrast agent is applied. This initial search can be conducted at low, fundamental frequencies and at transmit power levels (as indicated by the mechanical index or MI of the transmit beams) which are relatively high for good penetration. When the tumor is captured within the image, the clinician will switch the system to receive in the harmonic mode, and to transmit low MI beams to minimize bubble destruction. However, these changes will often cause the tumor to disappear from sight. This is because the clinician is relying upon the harmonic response of tissue to visualize the tumor prior to administration of the contrast agent, and there is little detectable tissue harmonic response at greater depths for MI's below 0.2–0.3. Consequently, it would be desirable to be able to conduct such a procedure without loss of visualization of the tumor prior to and while the contrast agent is being administered, but without transmitting high MI beams that would disrupt the microbubbles of the contrast agent.

In accordance with the principles of the present invention, an ultrasonic diagnostic imaging system and method are provided which enable harmonic imaging at low MI's and at deeper imaging depths. A transmit beam includes two frequency components, a low frequency fundamental component and a high frequency fundamental component which is at approximately the harmonic frequency of the low frequency component. At shallow and intermediate depths the system receives sufficient harmonic energy to image with the harmonic component, but at deeper depths the high frequency fundamental echoes provide signal levels for imaging, particularly in the case of low level transmit signals, as these signals do not suffer from the quadratically diminished signal levels of the nonlinear harmonic echoes. In a preferred embodiment a second pulse is transmitted with a different phase or frequency at the lower fundamental frequency so that the low fundamental frequency components of the returning echoes of the two pulses can be canceled by pulse inversion and the harmonic components reinforced by the two echo receptions.

In the drawings:

FIG. 1 illustrates in block diagram form an ultrasonic diagnostic imaging system constructed in accordance with the principles of the present invention;

FIGS. 2a and 2b illustrate two beam transmitters suitable for use in the embodiment of FIG. 1;

Figure 3:
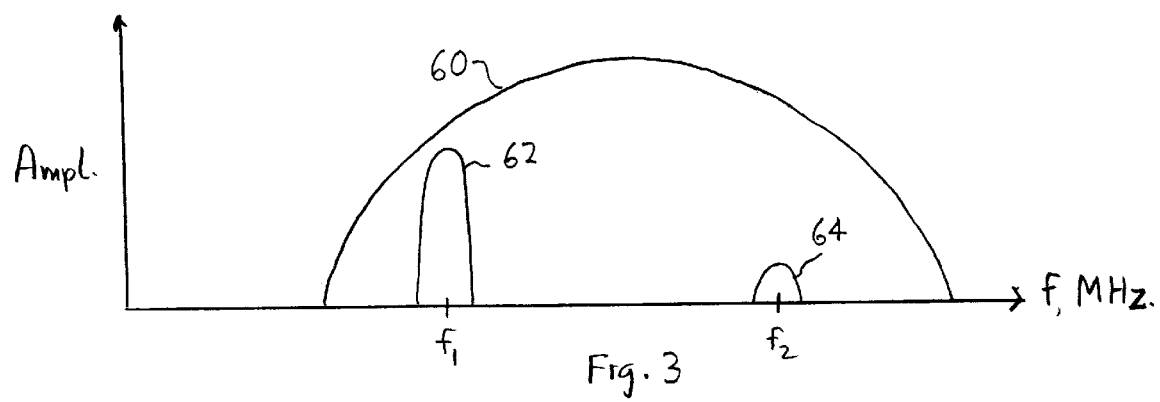
FIG. 3 illustrates the transmit frequency bands of a pulse transmitted in accordance with the principles of the present invention, in relation to a transducer passband.

Referring first to FIG. 1, an ultrasound system constructed in accordance with the principles of the present invention is shown in block diagram form. This system operates by scanning a region of the body being imaged with ultrasonic transmit beams which can have multiple frequency components $f_1$, $f_2$, etc. As each beam is transmitted along its steered path through the body, the beam returns echo signals with linear and nonlinear (fundamental and harmonic) components corresponding to the transmitted frequency components. The multiple frequency components are modulated by the nonlinear effects of the tissue through which the beam passes or the nonlinear response of a contrast agent microbubble encountered by the beam.

The ultrasound system of FIG. 1 utilizes a transmitter 16 which transmits single band or multiple frequency band beams for the return of fundamental and harmonic echo components from scatterers within the body. The transmitter is coupled by a transmit/receive switch 14 to the elements of an array transducer 12 of a scanhead 10. The transmitter is responsive to a number of control parameters which determine the characteristics of the transmit beams, as shown in the drawing, including the frequency components of the transmit beam, their relative intensities, and the phase or polarity of the transmit signals.

The transducer array 12 receives echoes from the body containing fundamental and harmonic frequency components which are within the transducer passband. These echo signals are coupled by the switch 14 to a beamformer 18 which appropriately delays echo signals from the different transducer elements then combines them to form a sequence of fundamental and harmonic signals along the beam from shallow to deeper depths. Preferably the beamformer is a digital beamformer operating on digitized echo signals to produce a sequence of discrete coherent digital echo signals from a near field to a far field depth of field. The beamformer may be a multiline beamformer which produces two or more sequences of echo signals along multiple spatially distinct receive scanlines in response to a single transmit beam. The beamformed echo signals are coupled to a nonlinear signal separator 20. The separator 20 may be a bandpass filter which passes a selected fundamental or harmonic passband to the relative exclusion (attenuation) of the transmitted fundamental band. In the illustrated embodiment the separator 20 is a pulse inversion processor which separates the nonlinear signals (even harmonics) which are reinforced, while fundamental signals cancel. Since second harmonic frequency signals are developed by nonlinear effects, they may advantageously be separated by pulse inversion processing. For pulse inversion the transmitter uses the variable transmit parameter which is the phase (or polarity) of the transmit pulse as shown in the drawing. The ultrasound system transmits two or more beams of different transmit polarities or phases. For a two pulse (two transmit event) embodiment, the scanline echoes received in response to the first transmit pulse are stored in a Line1 buffer 22. The scanline echoes received in response to the second transmit pulse are stored in a Line2 buffer 24 and then combined with spatially corresponding echoes in the Line1 buffer by a summer 26. Alternatively, the second scanline of echoes may be directly combined with the stored echoes of the first scanline without buffering. As a result of the different phases or polarities of the transmit pulses, the out of phase fundamental (linear) echo components will cancel and the nonlinear harmonic components, being in phase, will combine to reinforce each other, producing enhanced and separated nonlinear second harmonic (nonlinear) signals. The harmonic signals may be further filtered by a filter 30 to remove undesired signals such as those resulting from operations such as decimation. The signals are then detected by a detector 32, which may be an amplitude or phase detector. The echo signals are then processed by a signal processor 34 for subsequent grayscale, Doppler or other ultrasound display, then further processed by an image processor 36 for the formation of two dimensional, three dimensional, spectral, parametric, or other image display. The resultant display signals are displayed on a display 38.

FIGS. 2a and 2b illustrate two detailed embodiments of the transmitter 16 of FIG. 1. In the embodiment of FIG. 2a, the waveforms for the different frequency components of a multi-component transmit pulse are formed separately in digital operations, then combined to form a composite multifrequency transmit signal for application to a transducer element. An $f_1$ generator 42 produces the $f_1$ transmit signal component and an $f_2$ generator 44 produces the $f_2$ transmit signal component. The generators produce their respective transmit waveforms in response to input control parameters such as $f_1$ Sel. and $f_2$ Sel. shown in the drawing which determine the $f_1$ and $f_2$ frequency components of the transmitted beam. Other variable input parameters (not shown) may be intensity parameters a and b, and phase or polarity parameters for pulse inversion transmit signals. Alternatively, the output waveforms produced by the generators 42 and 44 may be varied in amplitude and phase or polarity before or after being combined by a combiner 46 into a composite transmit pulse which contains the multiple transmit frequency components. In FIG. 2a the waveforms produced by the generators are weighted by digital weighting processor circuits 43 and 45 which apply the weighting factors a and b to the generated waveforms. The weighting circuits can take the form of digital multipliers and the sign of the weighting factor (+1,−1) can be used to control the polarity of the output waveform. The composite transmit pulse is applied to a D/A converter 48 for conversion to an analog signal, which may be further amplified and filtered as desired and used to drive a transducer element 12'.

FIG. 2b illustrates a second transmitter embodiment in which single frequency or composite multifrequency transmit signals are produced in advance, then stored in a waveform library 50, which may be in the form of a digital memory. When a particular single frequency or multifrequency transmit pulse is desired it is selected from the library 50, weighted by a weighting circuit 51, and stored in a transmit register 52. When the transmitter is triggered to transmit a beam the stored waveform is shifted out of the transmit register 52 by a clock signal CLK, converted to an analog signal by the D/A converter 48 and applied to the transducer element 12'. The amplitude of the transmit pulse may be varied by either a digital multiplier preceding the A/D converter such as one used in the weighting circuit, or by an analog amplifier following the A/D converter, and may be filtered in either the analog or digital domain as desired. The individual frequency components may not be separately adjusted in amplitude following the transmit register 52 as the waveform is already a composite at that point in this embodiment.

It will be appreciated that the beam transmitted by the transducer array is steered in a desired beam direction and focused at a desired depth of focus, both of which are effected by the timing of application of transmit waveforms to different elements of the transducer array. Accordingly a number of transmit channels such as those shown in FIG. 2a or 2b are employed in the transmitter, one for each differently timed transmit waveform. The transmit channels may use the same transmit waveform but the times at which the waveforms of the channels are applied to the transducer elements are varied by the time delay profile needed for steering and focusing from the active elements of the transmit aperture.

Figure 4:
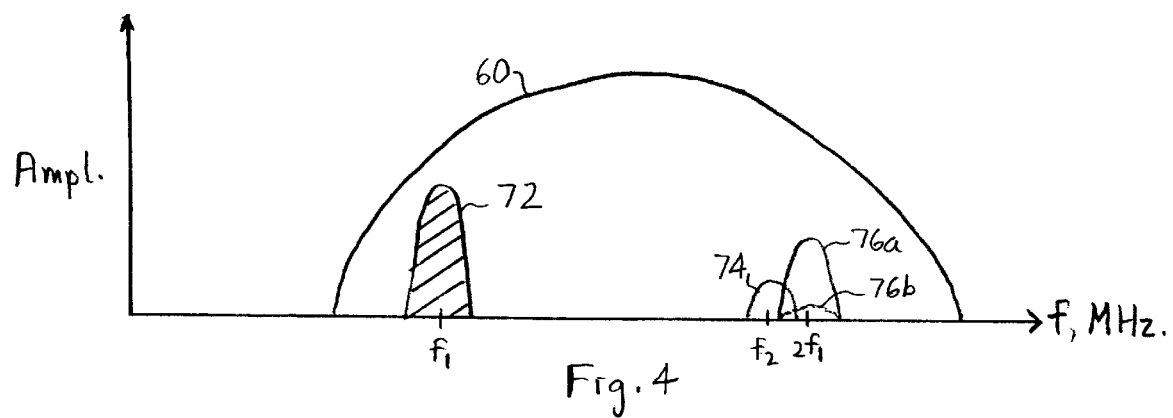
FIG. 4 illustrates the bands of the signals received in response to transmit pulses as illustrated in FIG. 3.

In accordance with the principles of the present invention, a preferred transmit pulse includes two frequency components as shown in FIG. 3, one developing a harmonic response and the other providing a fundamental frequency response in the same band of receive frequencies as the harmonic response of the first transmit frequency. The curve 60 represents the passband of a transducer which transmits ultrasound pulses containing energy in two frequency bands 62 and 64 located about frequencies $f_1$ and $f_2$, where the band 64 is in the vicinity of a harmonic band of band 62. The echoes received in response to a transmit pulse with these frequency components will have frequency components as shown in FIG. 4. The band 72 of frequencies located about frequency $f_1$ are fundamental (linear) frequency components returned from targets in the body. In a similar manner the high frequency transmit band 64 will return linear echo signals at the fundamental frequencies of the transmit band 64, as shown by the band 74 located about the frequency $f_2$. In addition there are second harmonic (nonlinear) return signals from the transmit band 62, which are located in a band 76, located about frequency $2f_1$. If the target returning the echo signals is a strong harmonic reflector such as a nonlinear contrast agent, the second harmonic signals will be relatively strong, as indicated by amplitude 76a. However, if there is no strong nonlinear reflector at the target, only a small harmonic return from tissue distortion will appear, as indicated by amplitude 76b.

This illustrates the condition described at the outset of this patent, the example of the loss of image detail when imaging a liver tumor. Initially, prior to the injection of a contrast agent, the liver can be imaged using pulses of a relatively high MI in the harmonic mode, with tissue harmonic distortion providing nonlinear return signals to visualize the tumor without clutter from nearfield scattering. When the tumor has been clearly located in the image the clinician will apply the contrast agent and reduce the transmit power to a low MI to avoid disrupting the microbubbles with high acoustic energy. The contrast agent will be clearly visible in real time at a low MI because the echo signals from the strongly nonlinear acting contrast agent will have amplitudes as indicated by 76a in FIG. 4. But prior to arrival of the contrast agent in the liver, the liver will be harder to visualize and the tumor may be completely indistinguishable in the image, because the amplitude of the tissue harmonic return signals will fall off quadratically as a function of the reduction of the transmit power (the reduced MI). The harmonic signals from the tumor in the absence of the contrast agent will decline to levels indicated by 76b, and may recede below the noise threshold of the system. This problem is exacerbated when imaging at considerable depths, because the relative higher frequency harmonic return signals will be severely affected by depth dependent attenuation.

An embodiment of the present invention overcomes this problem by providing higher amplitude echo signals in the band 74, resulting from the transmit pulses at frequency $f_2$. The echoes in the band 74 are not harmonic, but fundamental echoes, and are only linearly affected by decreases in transmit power. While the higher $f_2$ frequency will be affected by depth dependent attenuation to a greater degree than a lower frequency such as $f_1$, these echoes will not suffer the quadratic decline in intensities as harmonic components would. Thus, prior to arrival of the contrast agent the clinician can continue to visualize the tumor with echoes in the band 74 even at low MI transmission, until the vasculature of the tumor lights up with echoes from the contrast agent in band 76a.

The amplitude relationship of the transmitted components in bands 62 and 64 can be any desired relationship. In the preferred embodiment the higher frequency components are at a lower amplitude than the lower frequency components as indicated by the amplitudes of the bands in FIG. 3. This is because signals in band 64 are only being used for a fundamental return, not a harmonic return, unlike the returns from band 62. During reception the received signals are filtered to eliminate fundamental components in the band 72, as indicated by the shading of the band 72. Imaging is then done with the higher frequency components in the bands 74, 76. High pass filtering the returning echoes will eliminate clutter from the higher amplitude signals in band 72, which can manifest itself as clouding in the deeper depths as a result of scattering in the near field. By keeping the transmitted components in band 64 to a relatively low level, relatively little clutter will be created by these components, a characteristic which is aided by depth dependent attenuation of scattering from the higher frequency signals.

It is also possible to remove the fundamental signals of band 72 while leaving the signals in the higher bands 74, 76 by the use of pulse inversion. Pulse inversion is described in U.S. Pat. No. 6,319,203, and uses the transmission of two or more differently modulated pulses. As explained in that patent, the modulation can be phase modulation, amplitude modulation, or polarity modulation. Echoes from the transmissions are combined in a way which utilizes the modulation difference to cause linear components in the echo signals to cancel each other while nonlinear components reinforce each other. A preferred two pulse transmit sequence for pulse inversion in an embodiment of the present invention is (+) $a \sin \omega_1 t + b \sin \omega_2 t$ and (−) $a \sin(\omega_1 t + \pi)$ where the frequency $\omega_2 t$ is approximately or exactly twice the frequency $\omega_1 t$. The relationship of a and b can be b=a, b>a, b<a, but is preferably b<<a. It should also be noted that while the phase difference of the two low frequency ($\omega_1 t$) components is preferably 180°, it can be other relationships which result in less than complete linear signal cancellation. In a constructed embodiment, where the low and high frequency components were 1.7 MHz and 3.5 MHz, respectively, a was set to 1.0 and b was set to 0.05. When the echoes from these two transmit pulses are combined, the fundamental (linear) components $\omega_1 t$ cancel, the second harmonic of the fundamental components $\omega_1 t$ additively combine and reinforce each other, and the fundamental (linear) components of $\omega_2 t$ remain and are unaltered by the combining process.

Figure 5A:
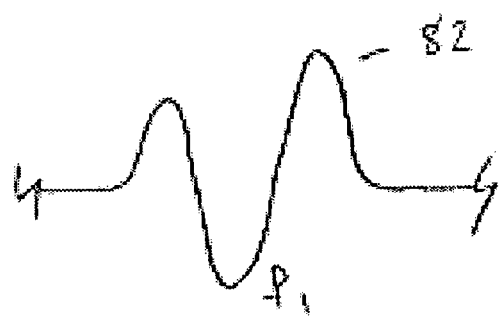
FIGS. 5a through 5d illustrate the frequency components and waveforms of a two pulse sequence by which the lower fundamental frequency may be canceled and its harmonics reinforced.
Figure 5B:
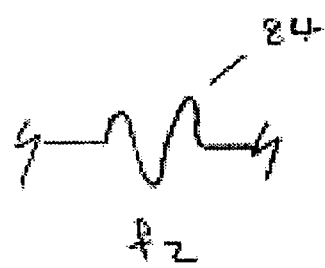
Figure 5C:
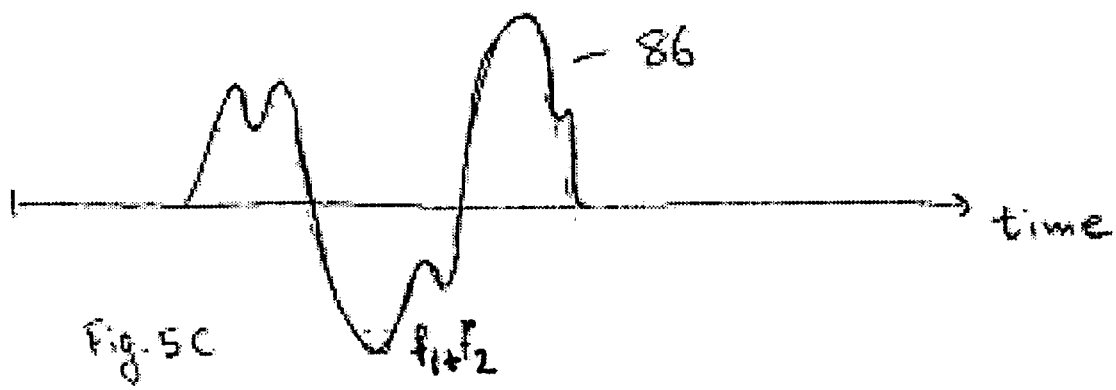
Figure 5D:
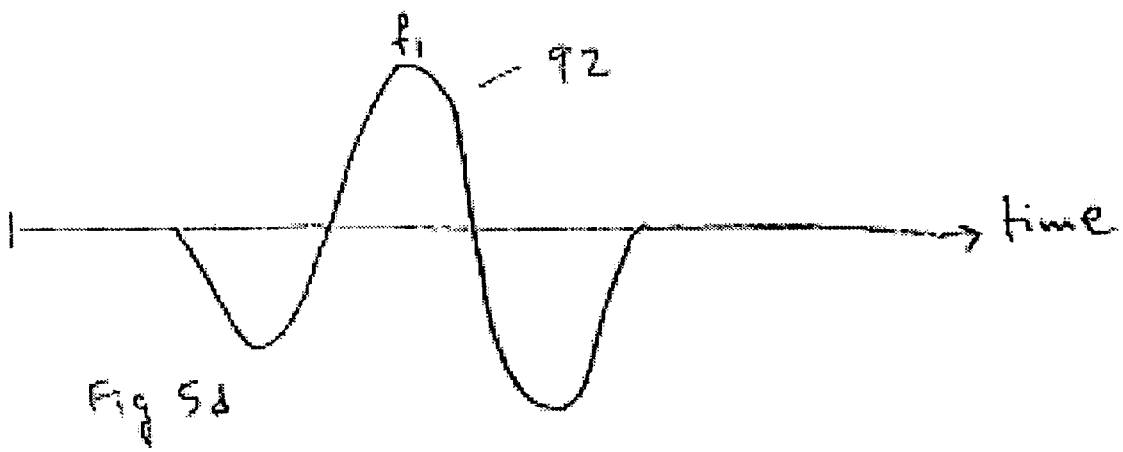

An example of the waveforms of a two pulse sequence of the present invention is illustrated in FIGS. 5a through 5d. FIGS. 5a and 5b illustrate the frequency components of the first (+) transmit pulse, which exhibits a low frequency $f_1$ fundamental component 82 and a high frequency $f_2$ fundamental component 84. The amplitude of the component 84 is much less than that of the component 82 to reduce clutter at deeper depths of imaging. A composite waveform 86 of frequencies $f_1+f_2$ is shown in FIG. 5c. The second (−) transmit pulse is shown in FIG. 5d, and includes a fundamental frequency component 92 which is the inverse (180° phase difference) of component 82. When echoes from these transmit pulses are combined, the linear components from transmit components 82 and 92 will cancel by reason of their phase or polarity difference. The echo from component 84 has no corollary in the second echo, and hence the linear echo component from transmit component 84 will remain. The fundamental components 82 and 92 will both result in second harmonics in the vicinity of frequency $f_2$, at or around the frequency of the fundamental echo from high frequency component 84. The second harmonics will reinforce each other by virtue of their quadratic characteristic. Thus, pulse inversion combination will leave both harmonics of the low frequency transmit pulses 82 and 92 and a fundamental linear component of the high frequency pulse component 84 for imaging.

It will be appreciated that if pulse component 92 is transmitted to be identical to pulse component 82, harmonic separation will be effected by a subtractive rather than an additive process.

Other variations of the present invention will be apparent to those skilled in the art. For instance, the frequency of the higher frequency transmit component may be chosen to be located in the vicinity of the receive frequency of a nonlinear component of the fundamental frequency which is other than the second harmonic frequency. The higher frequency may be chosen to be located at a higher order harmonic frequency, a fractional harmonic or a subharmonic frequency. In such a case the user will decide which nonlinear component of the basic fundamental frequency is desired for imaging, then align the other transmit component to have a fundamental frequency which is aligned with the nonlinear signal frequency chosen.

What is claimed is:

1. A method of harmonic ultrasonic imaging comprising:
    transmitting ultrasonic waves into a subject which comprise a first fundamental frequency component which is to produce a nonlinear receive frequency component and a second fundamental frequency component which is to produce a fundamental frequency component in the vicinity of the nonlinear receive frequency;
    receiving echo signals in response to the transmitted waves which include the nonlinear receive frequency component and a fundamental frequency component in the vicinity of the nonlinear receive frequency; and
    forming an image using the received echo signals.

2. The method of claim 1, wherein transmitting comprises transmitting ultrasonic waves into a subject which comprise a first fundamental frequency component which is to produce a nonlinear receive frequency component and a second fundamental frequency component which is to produce a fundamental frequency component at the nonlinear receive frequency.

3. The method of claim 1, wherein transmitting comprises transmitting ultrasonic waves into a subject which comprise a first fundamental frequency component which is to produce a second harmonic receive signal component and a second fundamental frequency component which is to produce a fundamental frequency component in the vicinity of the second harmonic receive signal frequency.

4. The method of claim 1, wherein transmitting comprises transmitting ultrasonic waves of the form $a \sin \omega_1 t + b \sin \omega_2 t$, where $a > b$.

5. The method of claim 4, wherein transmitting comprises transmitting ultrasonic waves of the form $a \sin \omega_1 t + b \sin \omega_2 t$, where $a \gg b$.

6. The method of claim 4, wherein transmitting further comprises transmitting ultrasonic waves into a subject at a low MI of 0.5 or less.

7. The method of claim 6, wherein transmitting further comprises transmitting ultrasonic waves into a subject containing a nonlinear ultrasonic contrast agent.

8. The method of claim 7, wherein transmitting further comprises transmitting ultrasonic waves into a subject containing a nonlinear ultrasonic contrast agent at a relatively deep depth.

9. The method of claim 1, wherein transmitting further comprises transmitting ultrasonic waves from an ultrasonic transmitter in which the waveform resides in digital form.

10. A method of harmonic ultrasonic imaging comprising:
    transmitting first ultrasonic waves into a subject which comprise a first fundamental frequency component exhibiting a first modulation characteristic and a second fundamental frequency component exhibiting a frequency in the vicinity of a nonlinear receive frequency;
    receiving echo signals in response to the first ultrasonic waves;
    transmitting second ultrasonic waves into a subject which comprise a fundamental frequency component at the first fundamental frequency exhibiting a second modulation characteristic;
    receiving echo signals in response to the second ultrasonic waves;
    combining the received echo signals by pulse inversion; and
    forming an image using the combined echo signals.

11. The method of claim 10, wherein combining comprises producing a harmonic component of the first fundamental frequency and a fundamental component of the second fundamental frequency while diminishing first fundamental frequency components.

12. The method of claim 10, wherein transmitting further comprises phase modulation.

13. The method of claim 10, wherein transmitting further comprises polarity modulation.

14. The method of claim 10, wherein transmitting further comprises amplitude modulation.

15. The method of claim 10, wherein transmitting comprises transmitting first ultrasonic waves into a subject which comprise a first fundamental frequency component exhibiting a first modulation characteristic and a second fundamental frequency component exhibiting a frequency in the vicinity of the second harmonic frequency of the first fundamental frequency.

16. A method of harmonic ultrasonic imaging comprising:
    transmitting first ultrasonic waves into a subject which are of the form $a \sin \omega_1 t + b \sin \omega_2 t$;
    transmitting second ultrasonic waves into a subject which are substantially of the form $a \sin(\omega_1 t + \pi)$;
    receiving echoes in response to the transmitted wave;
    combining the echoes by pulse inversion; and
    forming an image using the combined echoes, wherein $\omega_2 t \equiv n \omega_1 t$ and $n \neq 1$.

17. The method of claim 16, wherein forming comprises forming an image using the combined echoes, wherein $\omega_2 t \equiv 2 \omega_1 t$.

18. A method for ultrasonically imaging a target location at a depth within a subject comprising:
    transmitting ultrasonic waves to the target location which contain first and second fundamental frequency components;
    forming an image from harmonic frequency components of the first fundamental frequency when an ultrasonic contrast agent is present at the target location; and
    forming an image from fundamental frequency components of the second fundamental frequency when an ultrasonic contrast agent is absent at the target location.

19. The method of claim 18, wherein the first step of forming comprises forming an image from second harmonic frequency components of the first fundamental frequency when an ultrasonic contrast agent is present at the target location.

20. The method of claim 18, wherein transmitting comprises transmitting ultrasonic waves to the target location which contain a first fundamental frequency component and second fundamental frequency component which is at a harmonic imaging frequency of the first fundamental frequency.

21. The method of claim 18, further comprising separating imaging components by pulse inversion.

* * * * *